(12) United States Patent
Morazzoni et al.

(10) Patent No.: US 6,297,218 B1
(45) Date of Patent: Oct. 2, 2001

(54) **PHOSPHOLIPID COMPLEXES PREPARED FROM EXTRACTS OF *VITIS VINIFERA* AS ANTI-ATHEROSCLEROTIC AGENTS**

(75) Inventors: Paolo Morazzoni; Ezio Bombardelli, both of Milan (IT)

(73) Assignee: Indena SpA, Milan (IT)

( * ) Notice: Subject to any disclaimer, the term of this patent is extended or adjusted under 35 U.S.C. 154(b) by 0 days.

(21) Appl. No.: 09/580,906

(22) Filed: May 31, 2000

Related U.S. Application Data

(63) Continuation of application No. PCT/EP98/07662, filed on Nov. 30, 1998.

(30) Foreign Application Priority Data

Dec. 4, 1997 (IT) .............................. MI97A2690

(51) Int. Cl.⁷ .................... A61K 31/70; A61K 31/685
(52) U.S. Cl. ................................. 514/25; 514/78
(58) Field of Search ................ 514/25, 78, 456, 514/733, 824; 424/195.1

(56) References Cited

U.S. PATENT DOCUMENTS 4,963,527   10/1990   Bombardelli et al. ............... 514/25
5,484,594 * 1/1996   Frangi et al. ...................... 424/195.1
5,607,965   3/1997   Kondo et al. ...................... 514/456

FOREIGN PATENT DOCUMENTS

0713706 A    5/1996   (EP) .
2092743 *    6/1970   (FR) .
1541469 *    2/1979   (GB) .

OTHER PUBLICATIONS

Lust, J. The Herb Book; pp. 659, 1974.*
K. Tebib, et al., "Antioxidant Effects of Dietary Polymeric Grape Seed Tannins in Tissues of Rats Fed a High Cholesterol–Vitamin E–Deficient Diet," *Food Chemistry*, vol. 59, No. 1, pp. 135–141 (1997).
E. Bombardelli, et al., "Biological Activity of Procyanidins from *Vitis Vinifera L.*," *Biofactors*, vol. 6, No. 4, pp. 429–431 (1997).

* cited by examiner

*Primary Examiner*—Jon P. Weber
*Assistant Examiner*—Patricia D. Patten
(74) *Attorney, Agent, or Firm*—Pennie & Edmonds LLP

(57) ABSTRACT

The phospholipid complex extracts of *Vitis vinifera* useful for the prevention and the treatment of atherosclerotic pathological conditions and are administered to a patient in need of such treatment.

10 Claims, No Drawings

PHOSPHOLIPID COMPLEXES PREPARED FROM EXTRACTS OF *VITIS VINIFERA* AS ANTI-ATHEROSCLEROTIC AGENTS

CROSS-REFERENCE TO RELATED APPLICATIONS

This application is a continuation of the U.S. National Stage designation of co-pending International Patent Application PCT/EP98/07662, filed Nov. 30, 1998.

FIELD OF THE INVENTION

The present invention relates to the use of phospholipid complexes of oligomeric proanthocyanidins containing from 2 to 7 catechin units extracted from *Vitis vinifera* for the preparation of medicaments for the treatment and the prophylaxis of atherosclerosis, and of myocardial and cerebral infarctions.

BACKGROUND OF THE INVENTION

The extracts of *Vitis vinifera* are already known and used in the therapy of cardiovascular disorders connected with venous insufficiency, in the treatment of impaired conditions of capillary permeability and resistance and in cicatrization. These extracts, which can be obtained from the seeds of the plant as described in British patent application 1,541,469 or in French patent application 2,092,743, are a mixture of polyphenols such as epicatechin and its polymerization products, in part esterified at the C-3 hydroxyl of the monomer with gallic acid. The phospholipid complexes of the extracts of *Vitis vinifera* are described in U.S. Pat. No. 4,963,527 and are at present commercially available under the trademark LEUCOSELECT. The extracts of *Vitis vinifera* detailed in the prior art are obtained by extraction with acetone, usually using an acetone-water mixed solution.

SUMMARY OF THE INVENTION

The present invention is directed to a method for the treatment of atherosclerosis or of myocardial or cerebral infarctions and an anti-atherosclerotic medicament therefor. The method for the treatment of atherosclerosis or of myocardial or cerebral infarctions includes administering a therapeutically effective amount of an extract of *Vitis vinifera*, preferably in a phospholipid complex, to a patient in need of such treatment. Advantageously, the extract can contain oligomeric proanthocyanidins having from about 2 to about 7 catechin units. In one embodiment, the unitary dosage and/or the therapeutically effective amount of the medicament ranges from 50 mg to 500 mg. In another embodiment, the unitary dosage and/or the therapeutically effective amount of the medicament can range from 266 mg to 500 mg.

In a preferred embodiment, the medicament is in the form of an orally administrable composition. Alternately or additionally, a pharmaceutically acceptable carrier, adjunct, or excipient may also be present. Preferably, the pharmaceutically acceptable carrier is a soft or hard gelatin capsule or a tablet. More preferably, the capsule or tablet may be administrable orally.

Another aspect of the present invention relates to an anti-atherosclerotic medicament that includes a therapeutically effective amount of one or more of the extracts or phospholipid complexes described herein. In a preferred embodiment, the medicament is in the form of an orally administrable composition. Alternatively or additionally, a pharmaceutically acceptable carrier, adjunct, or excipient may also be present. Preferably, the pharmaceutically acceptable carrier is a soft or hard gelatin capsule or a tablet.

DETAILED DESCRIPTION OF THE PREFERRED EMBODIMENTS

It has now surprisingly been found that the complexes prepared according to U.S. Pat. No. 4,963,527 exert, when administered systemically, preferably by the oral route, a marked anti-atherosclerotic activity and effect both in animals and in humans.

More specifically, it has been found that the phospholipid complexes of oligomeric proanthocyanidins containing from 2 to 7 catechin units extracted from *Vitis vinifera*, prevent or reduce the formation of atherosclerotic plaques in a dose-dependent relationship.

Such an activity was evidenced in rabbits fed with hypercholesterolemic diet, so as to induce atherosclerotic lesions similar to the human ones at the vascular level, particularly at the aortic arch, ventral aorta, carotids, and cerebral vessels. In a comparative model, a normal, or control, diet was compared to two hypercholeseterolemic diets, one without and one with the above mentioned phospholipid complexes. It was found that the phospholipid complexes may have changed the macroscopic and microscopic vascular condition, compared with untreated animals, by reducing both the number of atheromatous plaques and their severity, with a surprising vascular-tissular benefit. In another atherosclerosis model, the purpose of which was to examine cerebral protection, the vasal lumen of rabbit internal carotid was surgically reduced, while administering a hypercholesterolemic diet rich in saturated fats. As a result, a decrease in carotid obstruction was exhibited, as well as a reduction of vessel wall thickness, and an increased survival rate of the animals was evidenced. Furthermore, in atherosclerotic patients, a reduction in carotid obstruction due to atheromatous plaques and an improved carotid flow were observed, as evaluated by Doppler ultrasonography.

The phospholipid complexes of the proanthocyanidins extracted from *Vitis vinifera* can be used in suitable oral formulations, for example, such as tablets and soft or hard gelatin capsules, at dosages preferably from 50 mg to 500 mg, or alternately from 266 mg to 500 mg, administered preferably two to three times a day, depending on the severity of the ailment to be treated. The preparation of the pharmaceutical formulations can be carried out according to conventional techniques and may optionally include pharmaceutically acceptable carriers, adjuncts, or excipients.

EXAMPLES

Certain preferred embodiments of the present invention will be illustrated in greater detail by reference to the following examples and comparative examples, which are included to exemplify, but not to limit, the scope of the present invention.

Examples 1–3

Comparative Model for Assessing the Effect of the Phospholipid Complex of Extracts of *Vitis vinifera* in a diet on the Severity of Atherosclerosis in Rabbits Three groups of eight New Zealand rabbits each, were treated as follows:

Group (1): Control, normal diet

Group (2): Hypercholesterolemic diet (0.2% cholesterol)

Group (3): Hypercholesterolemic diet+phospholipid complex of extracts of *Vitis vinifera* (0.2% cholesterol+2% Leucoselect®).

After 8 weeks, during which cholesterol, LDL/VLDL, HDL and triglyceride levels were measured, the animals were sacrificed. The number, the size, and the distribution of the atherosclerotic lesions on the thoracic and abdominal sections of the aorta were evaluated. Aorta strips were fixed and stained with Sudan IV to better visualize the lesions and to help evaluate the vasal cholesterol and the content in oxidized cholesterol by gas chromatography.

The results reported in Table 1 clearly demonstrate that the treatment with phospholipid complexes of extracts of *Vitis vinifera*, as in Example (3), decreases in a statistically significant way the atherosclerotic lesions induced by hypercholesterolemic diet of Example (2) and more closely resembles the control diet of Example (1).

TABLE 1

| Treatment | area percent of the lesion |
|---|---|
| Group (1) | 1% |
| Group (2) | 27% |
| Group (3) | 5%* |

*$p < 0.01$ compared with Group (2)

Examples 4–6 describe capsules or tablets containing 50 mg to 500 mg of phospholipid complex of extracts of *Vitis vinifera*.

Example 4

Capsules Containing Phospholipid Complex of Extracts of *Vitis vinifera*

Composition:

| | |
|---|---|
| Complex of extract of *Vitis vinifera* with soy phosphatidylcholine | 200 mg |
| Lactose | 57 mg |
| Modified starch | 40 mg |
| Magnesium stearate | 3 mg |

Example 5

Gastro-resistant Tablets Containing Phospholipid Complex of Extracts of *Vitis vinifera*

Composition:

| | |
|---|---|
| Complex of extract of *Vitis vinifera* with soy phosphatidylcholine | 250 mg |
| Microcrystalline cellulose | 118 mg |
| Precipitated silica | 3 mg |
| Magnesium stearate | 4 mg |
| Methacrylic acid anionic polymer and esters thereof | 2 mg |
| Talc | 8 mg |
| Magnesium carbonate | 8 mg |
| Maize star | 5 mg |
| Gum arabic | 159 mg |

Example 6

Soft-gelatin Capsules Containing Phospholipid Complex of Extracts of *Vitis vinifera*

Composition:

| | |
|---|---|
| Complex of extract of *Vitis vinifera* with soy phosphatidylcholine | 266 mg |
| Peanut oil | 209 mg |
| Partially hydrogenated vegetable oils | 100 mg |
| Soy lecithin | 5 mg |

What is claimed is:

1. A method for the treatment of atheosclersis or of myocardial or cerebral infarctions, which comprises administering a therapeutically effective amount of a phospholipid complex to a patient in need of such treatment, wherein the phospholipid complex is a complex resulting from the reaction of flavonoids extracted from *Vitis vinifera* with phospholipids selected from the group consisting of soy lecithin egg lecithin, phospholipids from bovine and porcine brains and skins, and compounds of the formula:

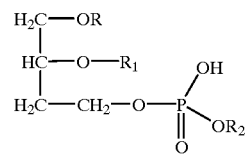

in which R and $R_1$, being identical or different, represent acyl groups from natural fatty acids and $R_2$ represents $(CH_2)N^+(CH_3), (CH_2)NH_2$, or $CH_2-CH(COOH)NH_2$, wherein the molar ratio of phospholipid to flavonoid is between 0.5 and 3.

2. The method of claim 1, wherein the extract comprises oligomeric proanthocyanidins that contain from 2 to 7 catechin units.

3. The method of claim 1, wherein the unitary dosage of the phospholipid complex to be administered ranges from 50 mg to 500 mg.

4. The method of claim 3, wherein the unitary dosage of the phospholipid complex to be administered is at least 266 mg.

5. The method of claim 1, wherein the phospholipid complex is administered orally.

6. The method of claim 1, wherein the phospholipid complex is administered with a pharmaceutically acceptable carrier, adjunct, or excipient.

7. The method of claim 6, wherein the pharmaceutically acceptable carrier is a soft or hard gelatin capsule or a tablet.

8. The method of claim 7, wherein the phospholipid complex is administered orally.

9. The method of claim 1, wherein the phospholipids are selected from the group consisting of soy lecithin and egg lecithin.

10. The method of claim 1, wherein the fatty acids are selected from the group consisting of palmitic, stearic, oleic, and linoleic acids.

* * * * *